United States Patent
Smith et al.

(10) Patent No.: US 8,037,882 B2
(45) Date of Patent: *Oct. 18, 2011

(54) CONDUIT WITH HEATED WICK

(75) Inventors: Daniel John Smith, Auckland (NZ); David Peter Baldwin, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 2421 days.

This patent is subject to a terminal disclaimer.

(21) Appl. No.: 10/684,917

(22) Filed: Oct. 14, 2003

(65) Prior Publication Data

US 2004/0118401 A1    Jun. 24, 2004

Related U.S. Application Data

(63) Continuation-in-part of application No. 09/886,835, filed on Jun. 21, 2001, now Pat. No. 6,662,802.

(30) Foreign Application Priority Data

Jun. 21, 2000  (NZ) .......................... 505355
Dec. 20, 2000  (NZ) .......................... 509040

(51) Int. Cl.
  *A61M 15/00*  (2006.01)
  *A61M 16/00*  (2006.01)
  *A61M 11/00*  (2006.01)
  *F24J 3/00*   (2006.01)
  *A62B 18/08*  (2006.01)
  *A62B 7/10*   (2006.01)

(52) U.S. Cl. ......... 128/203.16; 128/200.24; 128/204.17; 128/204.18; 128/201.13; 128/206.14; 128/200.18; 128/203.17; 128/203.26; 128/203.27; 128/205.12

(58) Field of Classification Search ............. 128/200.24, 128/204.17, 204.18, 201.13, 203.16, 206.14, 128/200.18, 203.17, 203.26, 203.27, 205.12, 128/911, 912

See application file for complete search history.

(56) References Cited

U.S. PATENT DOCUMENTS

| | | |
|---|---|---|
| 3,912,795 A | 10/1975 | Jackson |
| 4,048,993 A | 9/1977 | Dobritz |
| 4,265,235 A | 5/1981 | Fukunaga |
| 4,327,718 A | 5/1982 | Cronenberg |
| 4,337,800 A | 7/1982 | Carlson et al. |
| 4,343,672 A | 8/1982 | Kanao |
| 4,462,397 A | 7/1984 | Suzuki |
| 4,463,755 A | 8/1984 | Suzuki |
| 4,682,010 A | 7/1987 | Drapeau et al. |

(Continued)

FOREIGN PATENT DOCUMENTS

GB    2252515    *  8/1992

(Continued)

*Primary Examiner* — Patricia Bianco
*Assistant Examiner* — Nihir Patel
(74) *Attorney, Agent, or Firm* — Knobbe, Martens, Olson & Bear, LLP

(57) ABSTRACT

A conduit for a breathing circuit includes a heater associated, at least in part, with a hydrophilic layer. The purpose of the heater is to evaporate any condensed liquid collecting in the conduit, which is first sucked up by the hydrophilic layer. The heated wick reduces the risk of collected water being passed to the patient and causing choking fits or discomfit. It is preferred that the heated wick lies freely in the conduit to settle at low points in the conduit where condensation may collect.

8 Claims, 7 Drawing Sheets

U.S. PATENT DOCUMENTS

| | | | |
|---|---|---|---|
| 4,686,354 A * | 8/1987 | Makin | 392/472 |
| 4,708,831 A | 11/1987 | Elsworth et al. | |
| 4,722,334 A | 2/1988 | Blackmer et al. | |
| 4,771,770 A | 9/1988 | Artemenko et al. | |
| 4,773,410 A | 9/1988 | Blackmer et al. | |
| 4,808,201 A | 2/1989 | Kertzman | |
| 4,825,863 A | 5/1989 | Dittmar et al. | |
| 4,967,744 A | 11/1990 | Chua | |
| 5,042,500 A | 8/1991 | Norlien et al. | |
| 5,044,361 A | 9/1991 | Werner et al. | |
| 5,233,996 A | 8/1993 | Coleman et al. | |
| 5,284,160 A | 2/1994 | Dryden | |
| 5,392,770 A | 2/1995 | Clawson et al. | |
| 5,411,474 A | 5/1995 | Ott et al. | |
| 5,462,048 A | 10/1995 | Lambert et al. | |
| 5,501,212 A | 3/1996 | Psaros | |
| 5,586,551 A | 12/1996 | Hilliard | |
| 5,611,332 A | 3/1997 | Bono | |
| 5,630,409 A | 5/1997 | Bono et al. | |
| 5,704,344 A | 1/1998 | Cole | |
| 5,769,071 A | 6/1998 | Turnbull | |
| 5,894,839 A | 4/1999 | Rosenkoetter et al. | |
| 5,964,219 A | 10/1999 | Pekka | |
| 5,983,896 A | 11/1999 | Fukunaga et al. | |
| 5,992,413 A | 11/1999 | Martin, Jr. et al. | |
| 6,029,660 A | 2/2000 | Calluaud et al. | |
| 6,050,260 A | 4/2000 | Daniell et al. | |
| 6,078,730 A | 6/2000 | Huddart et al. | |
| 6,098,615 A | 8/2000 | Lloyd et al. | |
| 6,105,576 A | 8/2000 | Clawson et al. | |
| 6,116,235 A | 9/2000 | Walters et al. | |
| 6,167,883 B1 | 1/2001 | Beran et al. | |
| 6,349,722 B1 | 2/2002 | Gradon et al. | |
| 6,363,930 B1 | 4/2002 | Clawson et al. | |
| 6,367,472 B1 | 4/2002 | Koch | |
| 6,378,520 B1 | 4/2002 | Davenport | |
| 6,394,145 B1 | 5/2002 | Bailly | |
| 6,412,481 B1 | 7/2002 | Bienvenu et al. | |
| 6,474,335 B1 | 11/2002 | Lammers | |
| 6,516,798 B1 | 2/2003 | Davies | |
| 6,536,428 B1 * | 3/2003 | Smith et al. | 128/203.17 |
| 6,539,937 B1 | 4/2003 | Haveri | |
| 6,584,972 B2 | 7/2003 | McPhee | |
| 6,662,802 B2 * | 12/2003 | Smith et al. | 128/203.16 |
| 6,769,431 B2 * | 8/2004 | Smith et al. | 128/203.16 |
| 2002/0195104 A1 | 12/2002 | Fini et al. | |
| 2003/0028139 A1 | 2/2003 | Inoue | |

FOREIGN PATENT DOCUMENTS

| | | | |
|---|---|---|---|
| JP | 11323899 A * | 5/1998 | |
| JP | 11323899 A * | 11/1999 | |
| JP | 200024111 | 1/2000 | |

* cited by examiner

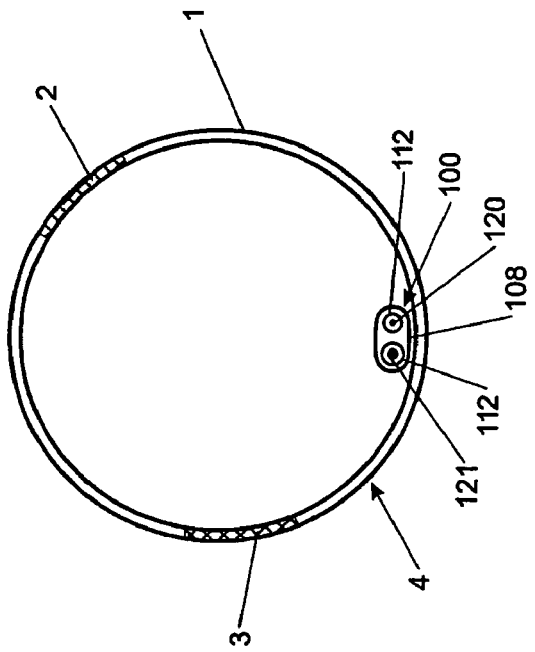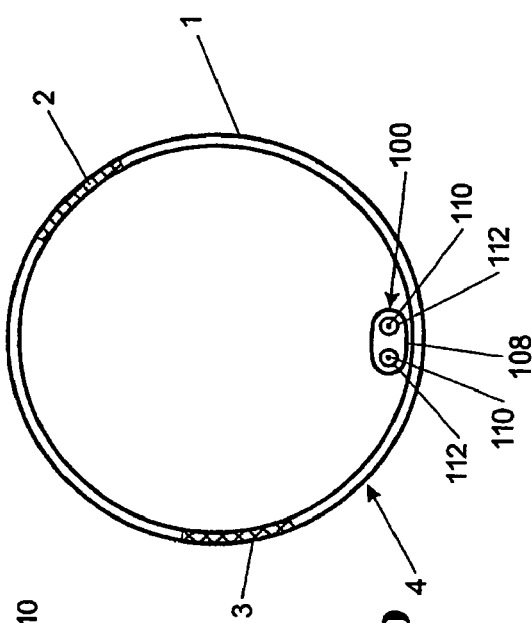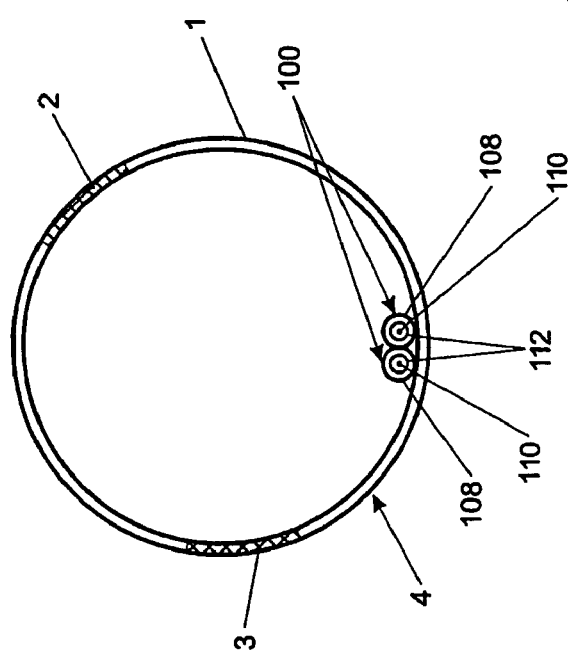

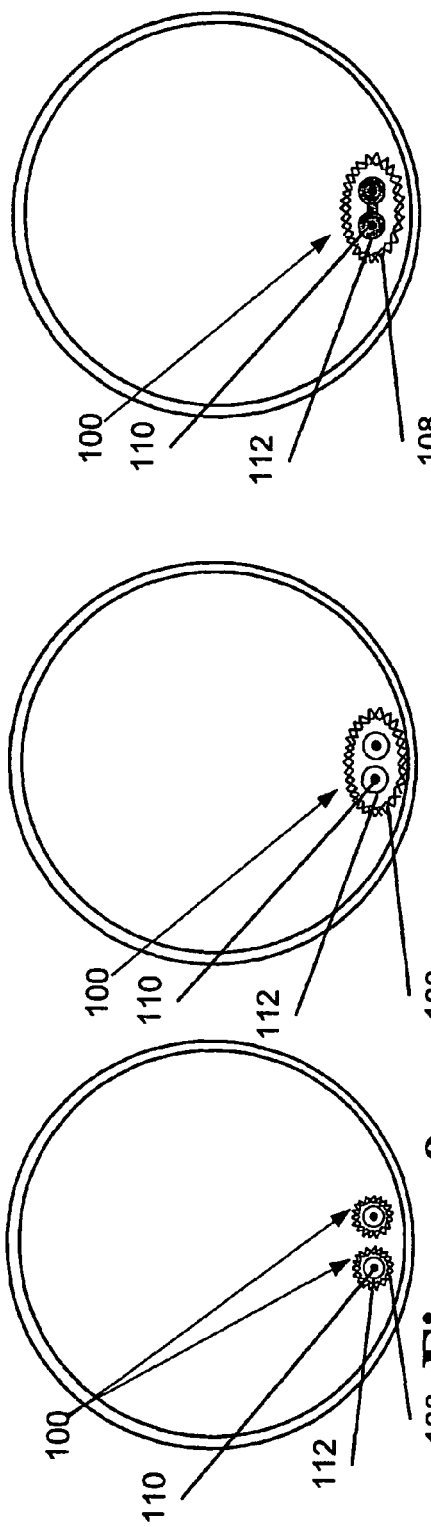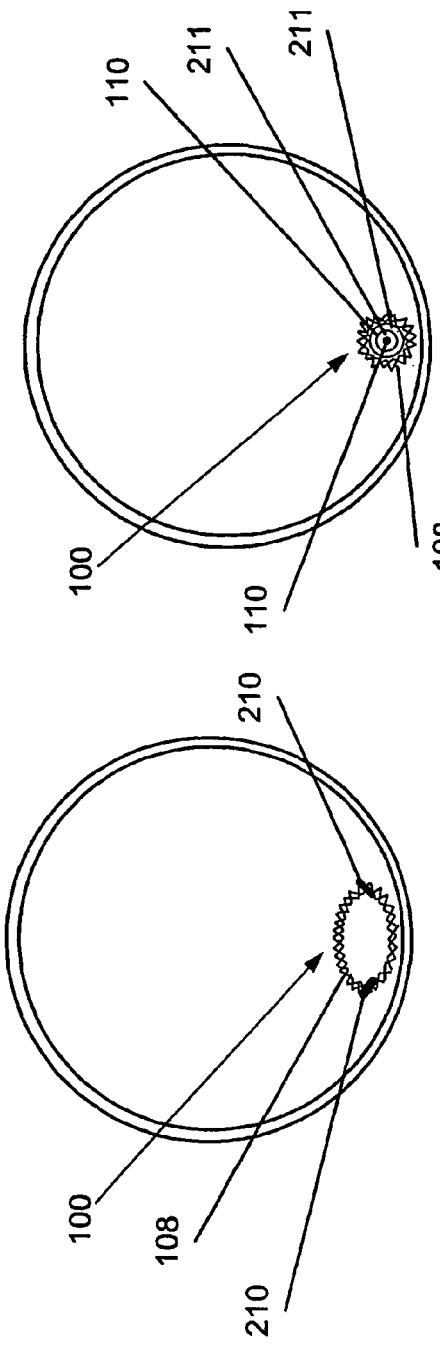

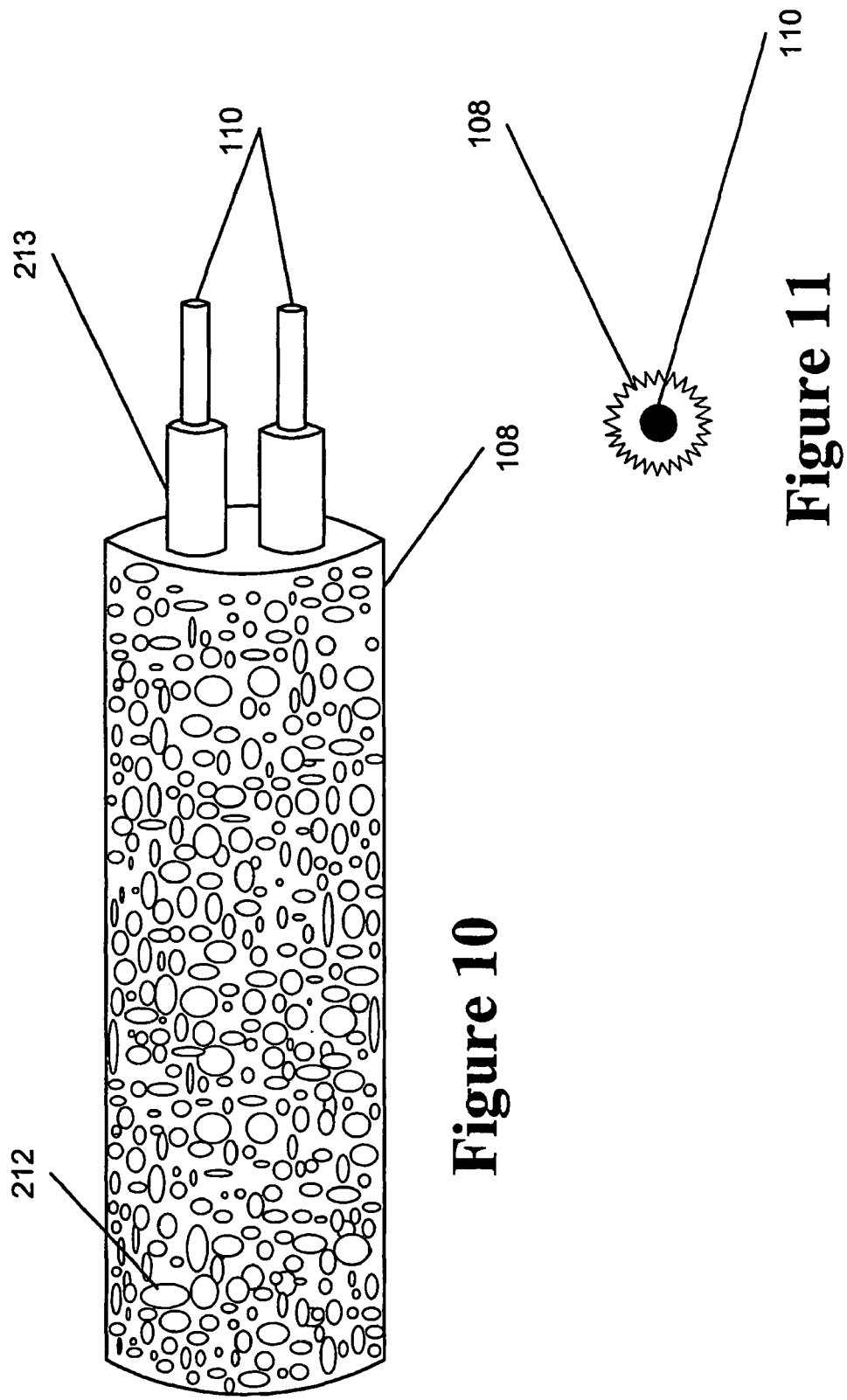

CONDUIT WITH HEATED WICK

This application is a continuation-in-part application of U.S. patent application Ser. No. 09/886,835 filed on Jun. 21, 2001, now U.S. Pat. No. 6,662,802, and entitled "Conduit With Heated Wick".

BACKGROUND TO THE INVENTION

1. Field of the Invention

The present invention relates to conduits and in particular to conduits for use in a breathing circuit.

2. Summary of the Prior Art

In assisted breathing, particularly in medical applications, gases having high levels of relative humidity are supplied and returned through conduits of a relatively restricted size. Build up of condensation on the inside wall of the conduit is a frequent result of this high humidity. In the prior art, attempts have been made to reduce the adverse effect of this condensation by either reducing the level of condensation or providing collection points in the conduit for draining condensed liquid from the conduit. Reducing the condensation has generally been by maintaining or elevating the temperature of the gases flow and/or of the conduit wall to reduce the formation of condensation.

SUMMARY OF THE INVENTION

It is an object of the present invention to provide a conduit, which will at least go some way towards improving on the above or which will at least provide the public and the medical profession with a useful choice.

In a first aspect the invention consists in a conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit.

In a second aspect the invention consists in a breathing circuit including an expiratory gases flow path and a heater located within said expiratory gases flow path and associated at least in part with a portion of hydrophilic material.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIG. 9 is a cross sectional view of a conduit including a heated wick according to a further embodiment of the present invention.

FIG. 10 is a cross sectional view of a conduit including a heated wick according to a still further embodiment of the present invention.

FIG. 11 is a cross sectional view of a conduit including a heated wick according to a still further embodiment of the present invention.

DETAILED DESCRIPTION

The present invention involves the provision of a heated wick within one of the lengths of conduit making up a breathing circuit. By heated wick we refer to a heater associated with a hydrophilic layer. The heated wick is disposed freely within the conduit so that at least part of it lays in low points of the conduit at which condensation accumulates. Accumulated condensation is absorbed by the hydrophilic layer and re-evaporated by heat from the heater.

Figure 1A:
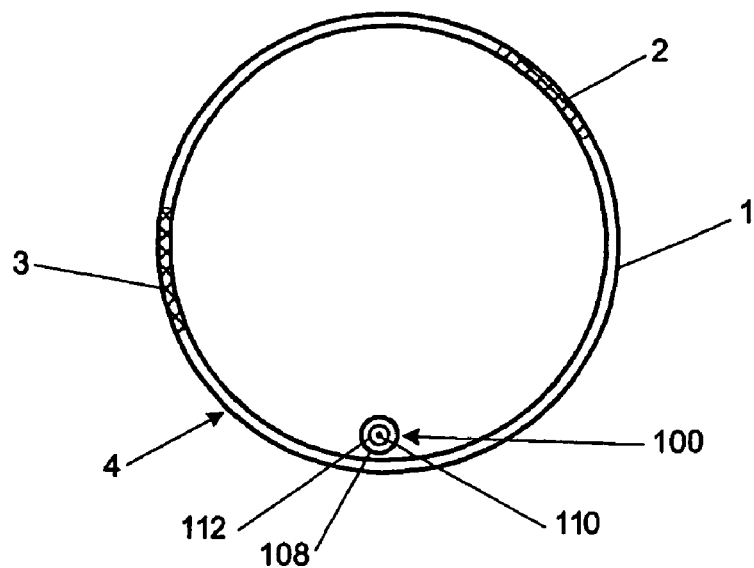
FIG. 1 is a cross sectional elevation of a conduit for the expiratory limb of a breathing circuit according to the present invention.
Figure 7:
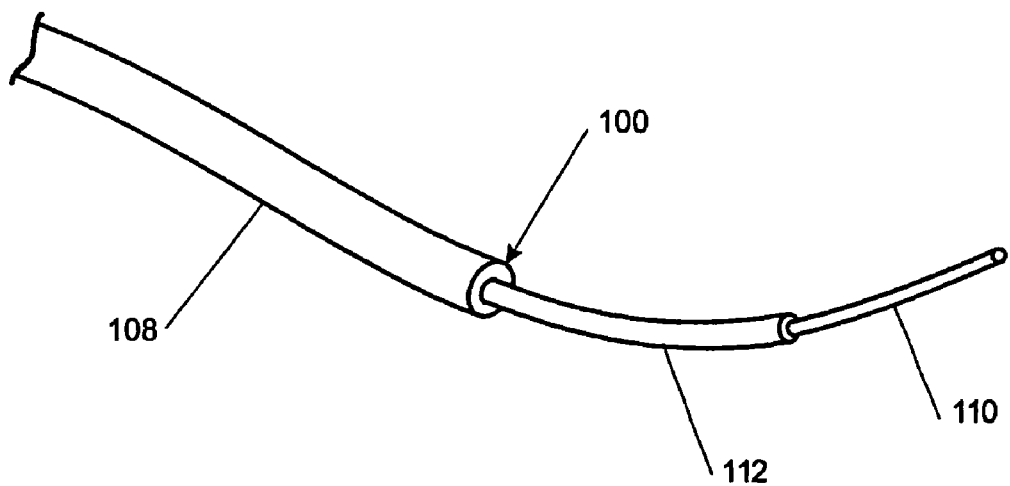
FIG. 7 is a cut-away perspective view of a heated wick according to a further aspect of the present invention.

As seen in FIGS. 1A and 7 the heated wick 100 is comprised of an outer hydrophilic layer 108, covering an inner insulating hydrophobic layer 112, which in turn covers a heater element 110. Any water that collects in the conduit 102 is attracted to and drawn into the hydrophilic layer 108, and is then re-vaporised as it is heated by the heater element 110. The intermediate hydrophobic insulating layer 112 is provided to electrically insulate the inner heater element 110 from the rest of the system.

Such a heated wick 100 as shown in FIG. 7 may be constructed by coextruding the hydrophobic insulating layer 112 and hydrophilic layer 108 onto the heater wire 110. Suitable materials for the hydrophilic layer include polyester or polyurethane foam, or a braid of hydrophilic material e.g cotton. Suitable materials for the hydrophobic insulating layer include polypropylene or silicone coatings.

An alternate form for the heated wick is shown in each of FIGS. 1b, 1c and 1d. In FIG. 1b the heated wick includes a looped back heater element 110, coated in a hydrophobic insulating layer 112, and the whole encased within a hydrophilic surrounding layer 108. In a further variation depicted in FIG. 1c the heater element is an electrical resistance heater and includes a length 120 of higher resistance and a length 121 of lower resistance, insulated from one another and joined at their remote ends. In a still further variation depicted in FIG. 1d the heated wick 100 is disposed in the conduit as a simple loop. Each of these variations provide both ends of the heated wick at the same end of the conduit, allowing a single connection of the heater element to an energising source. The embodiment of FIG. 1c has the additional advantage that the heater element voltage at the remote end will be lower than half the supply voltage, and with appropriate selection can be very close to zero.

Alternatively the hydrophilic layer 108 may achieve its hydrophilic (water attracting effect), through its physical structure and capillary action rather than an inherent property of the material composition. It is to be understood that references to the outer hydrophilic layer 108 throughout the specification may refer to the overall hydrophilic nature of the layer 108. The hydrophilic layer 108 may be constructed from a hydrophilic material composition or alternatively may be constructed from water resistant materials but have a physical structure configured so water 'soaks' into or is attracted to the layer 108 through capillary action. Alternative constructions of the surrounding hydrophilic layer 108 are shown in FIGS. 9a to 9d and FIGS. 10 and 11.

For example, as seen in FIG. 9a the heated wick 100 is comprised of an inner insulating layer 112 which covers a heater element 110. The heater element 110 and the insulating layer 112 are encased in an outer hydrophilic layer 108, which is comprised of a braided sheath. The braided filaments may be of a water resistant material such as polyethylene terepythalate (PET), polyethylene or polypropylene. In use, liquid water or condensate is drawn into the spaces between the filaments of the braided sheath by capillary action thus giving layer 108 a water attracting or hydrophilic effect.

An alternative form of the heated wick is shown in each of FIGS. 9b, 9c and 9d. The construction shown in FIG. 9b is analogous to that described previously and shown in FIG. 1b, except that the hydrophilic surrounding layer 108 is a braided sheath similar to that shown in FIG. 9a. A variation of the structure shown in FIG. 9b is shown in FIG. 9c. In this embodiment the hydrophobic insulating layer 112 encapsulates both the positive and negative heater wire strands together.

A further alternative form of the heated wick is shown in FIG. 9d. In this embodiment the heater wire(s) are provided by conductive strands 210 which are braided into the braided mesh. In this embodiment a pair of conductive heater wire strands 210 are coated in an electrical insulating material and braided into a mesh tube in order that the heated wick can attract water to itself through capillary action. It will be appreciated that a single heater wire or multiple wires may be advantageous.

FIG. 9e show a heated wick embodiment where the positive and negative heater wires are arranged co-axially. In this embodiment a pair of heater wires 110, are shown. Each heater wire is surrounded by an electrical insulating layer 211, and each is arranged co-axially. An outer water attracting braided sheath 108 surrounds the heater wires to give the construction a wicking effect due to capillary action.

Alternatives to the braided mesh embodiment are shown in FIGS. 10 and 11. In these embodiments the outer hydrophilic layer 108 is constructed from a water resistant material (for example PET) and attracts water into spaces and voids 212 on the outer surface of the layer 108 through capillary action. The hydrophilic layer 108, shown in FIG. 10 is formed from a partially foamed plastic layer which encases the insulated conductive wire(s). The outer layer is covered in voids or pores 212, in order that the heated wick can attract water to itself through capillary action. Alternatively, the outer layer may be formed by sintering. Heater element(s) 110 are imbedded in layer 108, and may also include an electrical insulating layer 213.

An alternative structure of a non-braided layer 108 constructed from a water resistant material is shown in FIG. 11. In this embodiment the outer layer 108 includes a number of grooves and/or fins in order to allow the wick to attract water though capillary action. The grooves may be substantially axial, annular, helical or knurled in a criss-cross fashion.

The heated wick may also be provided in both the inspiratory and expiratory conduits. In this case a single length of heated wick may run down the inspiratory conduit and back up the expiratory conduit, with the ends of the conduits being insufficiently close proximity to enable easy electrical connection to both ends.

The heated wick is provided with connections at its ends for connecting to an energising source. The ends of the wick may be directly electrically connected to electrical connectors in the connector of the tube or conduit. These connectors may for example be a socket for receiving a plug from a voltage source. Alternatively the heated wick may be a fixture of an assisted breathing device, such as a ventilator or humidifier, and may extend from within the breathing conduit connection port of the device, or be plugged into a socket within such port. Many other configurations for supplying power to the heated wick will also suggest themselves.

Figure 6:
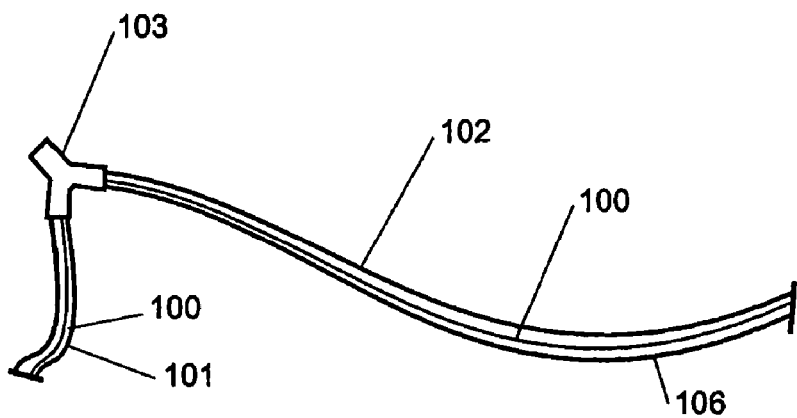
FIG. 6 is a representation of a breathing circuit with an expiratory limb fashioned according to the present invention and including a heated wick according to a further aspect of the present invention.

The heater element 110 is also effective to supply heat to the gases stream to reduce the overall level of condensation occurring within the conduit. At the same time any condensation that does occur is sucked up by the wick and re-evaporated by heat from the heater element 110. Accordingly where a heated wick is provided in the inspiratory arm of the breathing circuit humidity supplied to the gases stream prior to entry into the breathing circuit is not lost through condensation, instead being re-evaporated by the heated wick. This reduces the total humidification load of the breathing circuit as well as eliminating the requirement for conduit drainage ports.

Where the heated wick is provided in the expiratory conduit it eliminates the need for conduit drainage ports. Furthermore it provides additional advantages when used in conjunction with an expiratory conduit in which at least a part of the conduit wall is formed from a breathable material. Such an arrangement is shown in FIG. 6.

A breathable material, as used herein, is a material that allows the passage of water vapour without allowing the passage of liquid water or respiratory gases. Materials may be breathable due to their composition, physical structure a combination thereof.

One such breathable material is an activated perfluorinated polymer material having extreme hydrophilic properties. An example of this polymer material is marketed under the trade mark NAFION by DuPont Fluoro products of Fayetteville USA. This material is useful due to its extreme hydrophilic properties and due to its ability to be extruded, particularly to be co-extruded in combination with other plastic materials.

Alternative materials are also envisaged including:
(a) Hydrophilic thermoplastics,
(b) woven treated fabric products exhibiting breathable characteristics The preferred material is a hydrophilic polyester block copolymer formed into a homogeneous flat film. An example of such a film is sold under the brand SYMPATEX. This material is particularly suited to thin film productions.

An example of application of the conduit with heated wick is shown in FIG. 6. A heater element 110 coated with a hydrophilic layer, runs the length of the semi-permeable conduit 102 and the inspiratory conduit 101. During operation humidified gases are drawn through inspiratory conduit 101, then flow through the T connector 103, and are then delivered to the patient (not shown). When the patient expires the gases flow through the T connector 103, and then flow through the breathable expiratory conduit 102. The expiratory gases will be almost saturated with humidity and as the wall of the breathable expiratory conduit 102 will be relatively cool, some portion of the vapour in the gases will condense and therefore water will collect in the conduit and run towards the lowest point 106. As already mentioned such collection of water is undesirable and therefore the heated wick 100 is provided to revaporise the water that collects. This is particularly important where the breathable material is one, such as SYMPATEX, which transmits water vapour but does not transmit liquid water. While such materials are advantageous for their ability to stop harmful bacteria and viruses this advantage is offset by their inability to transmit liquid water. By re-evaporation of any collected water by the heated wick it can be transmitted through the breathable membrane in its vapour state.

Referring to FIG. 1, in one embodiment, the conduit 4 of the expiratory limb of a breathing circuit is formed having one or more longitudinal strips 2, 3 of breathable membrane as part of the wall 1 thereof.

Figure 8:
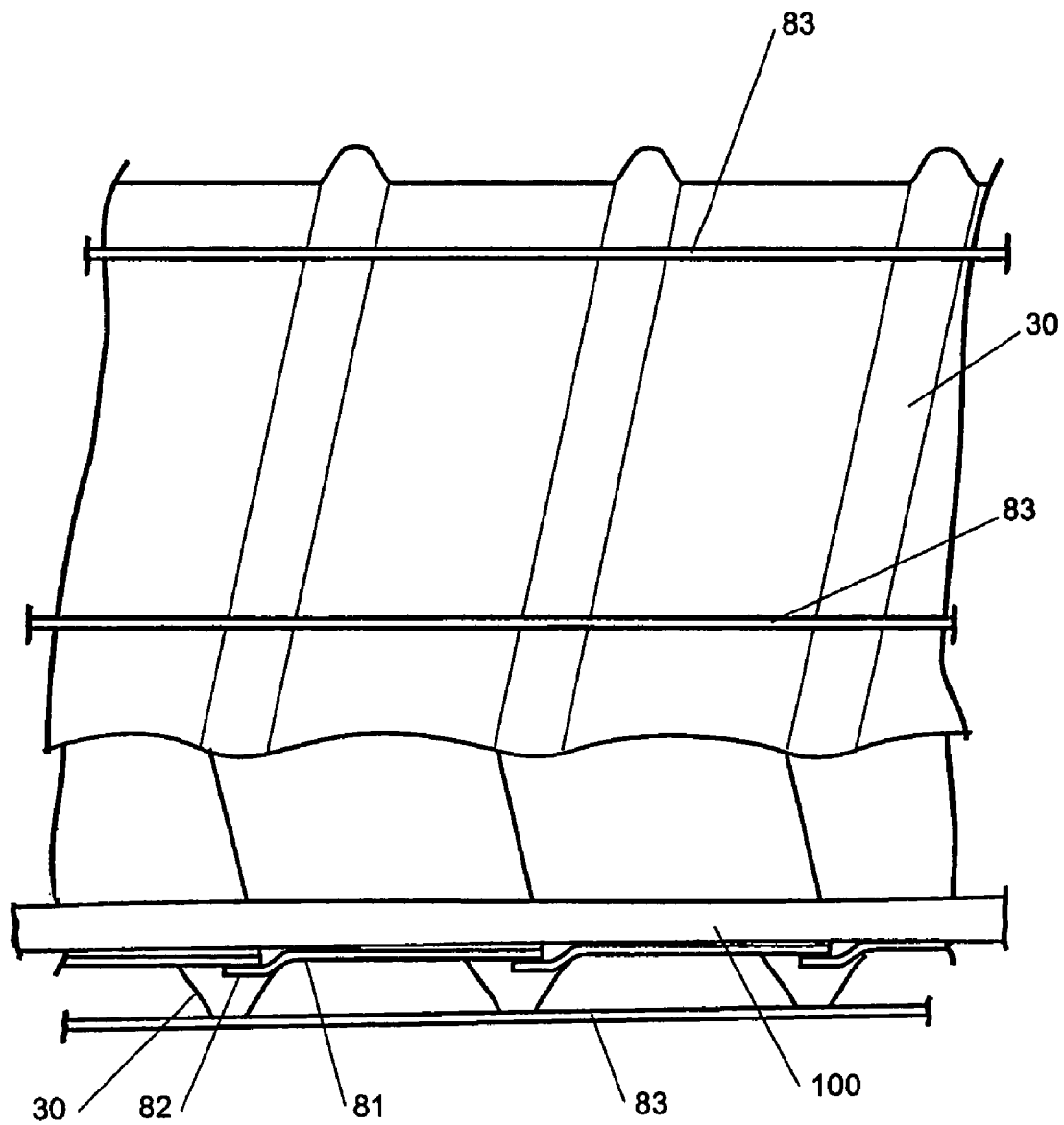
FIG. 8 is a side elevation partially in cross section of an expiratory limb conduit according to a further embodiment of the present invention.

Referring to FIG. 8 an alternative embodiment of the expiratory limb conduit is shown in which the entire flexible wall membrane of the conduit is formed from a breathable plastic membrane, extruded and wound helically with edges of adjacent turns sealed to one another.

Figure 4:
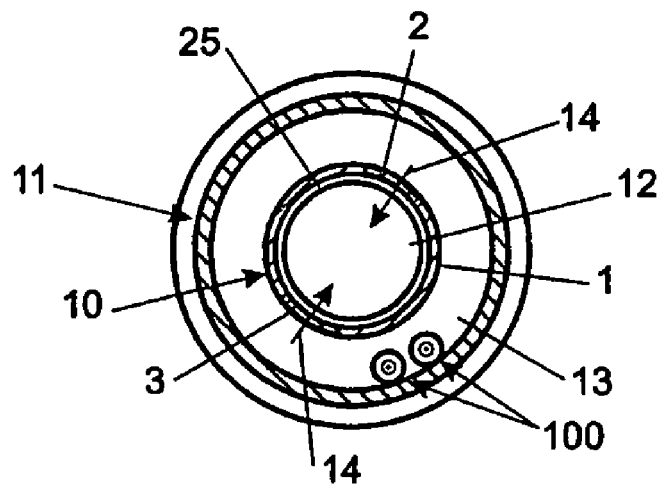
FIG. 4 is a cross sectional elevation of a coaxial breathing circuit according to a further embodiment of the present invention incorporating a heated wick in the expiratory gases flow path.
Figure 5:
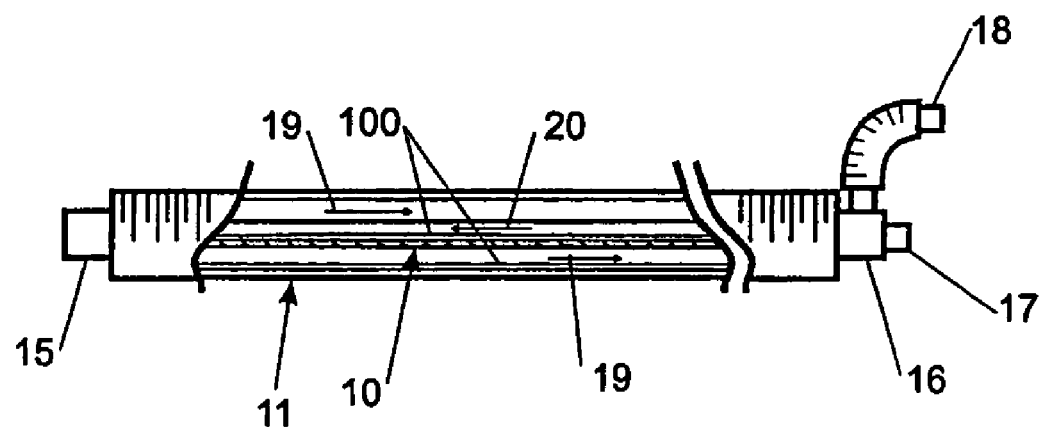
FIG. 5 is a side elevation in partial cross section of a coaxial breathing circuit including a heated wick in both the inspiratory and expiratory gases flow paths.

Referring to FIGS. 4 and 5, further aspects is shown in which an expiratory limb conduit according to the present invention is provided as a gases flow path of a coaxial conduit configuration, such that expiratory gases and inspiratory gases each flow in one of the inner conduit or the space between the inner conduit and the outer conduit and in use water vapour but not liquid water is transmitted from the expiratory gases passageway to the inspiratory gases passageway.

Figure 2:
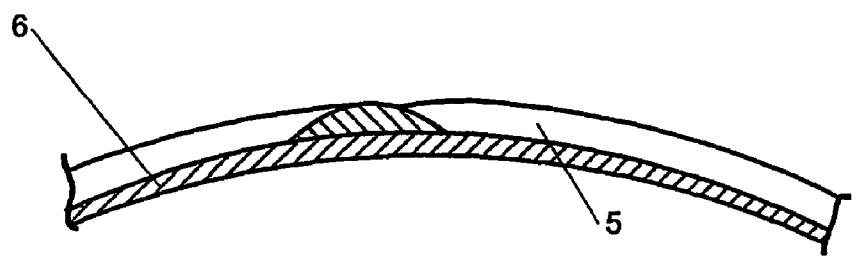
FIG. 2 is a cross sectional view of a section of conduit wall according to one possible construction.

Referring to FIGS. 2 & 8, spiral or helical internal (or external) reinforcing members 30, or a series of annular hoop reinforcing members, may be provided outside (or inside) the tubular membrane 6 to provide support to it. The helical, spiral or hoop supporting members may for example be formed from polymer plastic materials, such as the material used in the wall of the conduit (not being the breathable regions), or alternatively may for example be a metal wire support, such as drawn steel wire.

The conduit shown in FIG. 2 may be formed in any one of a number of methods. For example the tubular membrane 6 may be supplied in a continuous tube. Alternatively it might be supplied in tape form, which may result in the conduit of FIG. 8. Supplied as extruded tape 81, the membrane may be wound helically onto a former. The helical supporting rib 30, provided in a breathable molten state is then laid on the overlap between adjacent turns. The heat from the helical supporting rib 30 bonds the two adjacent strips with itself forming a flexible resilient conduit once cooled.

Referring to FIG. 8 an additional longitudinal reinforcement may be provided to alleviate the shortcomings of some of the breathable materials. This reinforcement may be in the form of a plurality of reinforcing threads 83. The threads 83 run parallel to the length of the conduit and are supported on the helical reinforcing ribs, spanning between them. As many threads may be provided. For example eight threads may be spaced around the circumference of the tube. The reinforcing threads 83 stop accidental stretching of the conduit, and providing they have some stiffness and the rib spacing is not to large, also reduce any longitudinal compression of the conduit under negative relative internal pressures.

Figure 3:
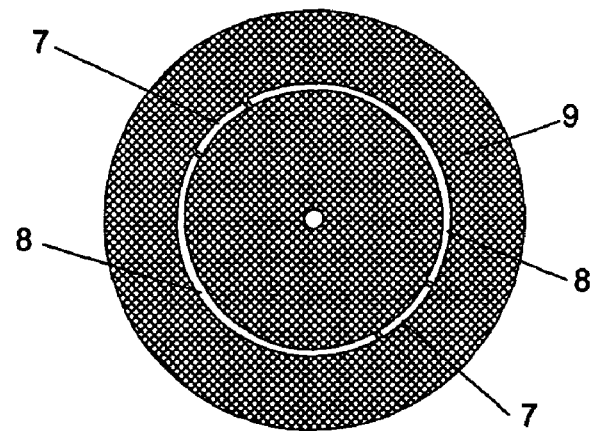
FIG. 3 is a cross sectional view of a co extrusion die head for extruding a conduit including two longitudinal strips of permeable material, similar to the conduit of FIG. 1.

Referring to FIG. 3 the conduit, such as that shown in FIG. 1, may alternatively be formed by co extrusion of the breathable material (where the material is a suitable extrudable material) with a plastic material forming the remainder of the conduit wall. A suitable co extrusion die 9 is depicted in FIG. 3 in which a pair of circumferential sections 7 of the die opening have the breathable plastic material extruded therethrough, and the remainder sections 8 of the annular extrusion opening have the non permeable plastic wall material extruded therethrough.

The purpose of the breathable region or regions of the conduit wall is to allow diffusion of water vapour (and for some materials liquid water) from the expiratory limb of the breathing circuit along the path thereof independent of specific drain locations. This eliminates the build up of condensation within the expiratory limb by drying the humidified gases during their flow through the expiratory limb. This furthermore reduces the humidity of the gases arriving at ancillary equipment, such as filters, ventilators and the like reducing the risk of condensation accumulation, thereby improving their operation.

In accordance with a further aspect of the invention, and as exemplified in FIGS. 4 and 5 the conduit incorporating one or more longitudinal strips of breathable membrane may further be incorporated in a coaxial breathing circuit as a passive humidification device. In particular referring to the cross section in FIG. 4 the coaxial breathing circuit may include an outer conduit 11 and an inner conduit 10. Preferably, for heat transfer reasons, the inner conduit 10 carries the inspiratory flow in the space 12 there within. The expiratory flow is carried in the space 13 between the inner conduit 10 and the outer conduit 11, and a doubled back heated wick 100 is provided in the expiratory flow space. The airflow configuration is indicated by arrows 20, 19 respectively in FIG. 5.

The inner conduit 10 is formed having one or more longitudinal strips 2, 3 of breathable membrane in the wall 1 thereof, as has previously been described with reference to FIGS. 1, 2 and 3. Thus humidity in the expiratory flow space 13 may pass through the sections 2, 3 of breathable membrane to humidify the inspiratory flow in inspiratory flow space 12.

The breathable membrane works on relative partial pressures of water vapour so, with the flows in a counter flow arrangement substantial passive humidification of the inspiratory flow can be achieved.

Referring to FIG. 5 a circuit configuration including the coaxial conduit depicted in FIG. 4 is represented, but with a heated wick 100 disposed in both of the inspiratory and expiratory flow paths (for example doubling back at the patient end connector 15). In this circuit the conduit has a patient end connector 15 and a ventilator end connector 16 having inspiratory port 17 and an expiratory port 18. The inspiratory 20 and expiratory 19 counter flows are indicated.

So in its broadest form the invention is a conduit for a breathing circuit which includes a heater associated, at least in part with a hydrophilic layer to attract liquid water or condensate to itself. The purpose of the heater is to evaporate any condensed liquid collecting in the conduit. The heated wick is not a humidifier and so no liquid is supplied directly to the hydrophilic material from outside said conduit. The heated wick reduces the risk of collected water being passed to the patient and causing choking fits or discomfit. It also improves the predictability of the humidity levels in the gases passed to the patient. It is preferred that the heated wick lies freely in the conduit to settle at low points in the conduit where condensation may collect.

Where the conduit in question is an expiratory conduit, or at least where the heated wick is located in an expiratory flow path of a breathing circuit, then the heated wick will have additional benefits where the conduit has at least of potion of its wall formed from breathable material for passive dehumidification of the expired gases. Because the breathable material will pass only vapour, evaporation of any condensed liquid within the conduit will allow that liquid to subsequently be passed.

Another aspect to the invention is the construction of the heated wick, which is preferably an elongate heating element covered with an inner hydrophobic insulating layer co-extruded with an outer hydrophilic layer.

It will be appreciated that the concepts encapsulated by the described and illustrated embodiments are not restricted to being combined only as described. For example the heated wick described with reference to FIGS. 6 and 7 may be used in the coaxial conduit of FIGS. 4 and 5 or the separate limbed conduit as in FIG. 6. Similarly the conduit incorporating the breathable membrane, whether it be the inner conduit of the coaxial configuration shown in FIGS. 4 and 5 or the stand alone expiratory limb of FIG. 6, may be formed as a co-extrusion as in FIGS. 1 and 3 or as an extruded tape as in FIG. 8 and with the breathable membrane being of a number of alternate materials. While some embodiments have been described as preferred and convey particular advantages over other embodiments many other combinations may prove commercially useful.

The invention claimed is:

1. A conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit, said hydrophilic layer being formed so as to absorb water due to its structure, wherein said conduit is an expiratory conduit and said heater is located in an expiratory flow path of said conduit and at least a length of said conduit has a conduit wall wherein at least a region of said conduit wall is of a breathable material.

2. A conduit as claimed in claim 1 wherein said at least a region is or are distributed over said length of said conduit.

3. A conduit as claimed in claim 1, wherein said hydrophilic layer is a braided sheath.

4. A conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit, said said hydrophilic layer being formed so as to absorb water due to its structure, said heater lying freely in said conduit to settle over at least some of its length at low points in said conduit where condensed water vapour may collect, wherein said conduit is an expiratory conduit and said heater is located in an expiratory flow path of said conduit and at least a length of said conduit has a conduit wall wherein at least a region of said conduit wall is of a breathable material.

5. A conduit as claimed in claim 4 wherein said at least a region is or are distributed over said length of said conduit.

6. A conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit, wherein said hydrophilic layer is a braided sheath.

7. A conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit, said hydrophilic layer being formed so as to absorb water due to its structure, wherein said hydrophilic layer is a braided sheath.

8. A conduit for a breathing circuit including a heater located within said conduit, said heater comprising an elongate heating element covered with an inner electrical insulating layer and at least partially covered with an outer hydrophilic layer, there being no means for direct supply of water or fluid to said hydrophilic layer from outside said conduit, said hydrophilic layer being formed so as to absorb water due to its structure, said heater lying freely in said conduit to settle over at least some of its length at low points in said conduit where condensed water vapour may collect, wherein said hydrophilic layer is a braided sheath.

\* \* \* \* \*